(12) United States Patent
Erpenbach et al.

(10) Patent No.: US 11,120,912 B2
(45) Date of Patent: Sep. 14, 2021

(54) COGNITIVE SYSTEMS FOR GENERATING PROSPECTIVE MEDICAL TREATMENT GUIDANCE

(71) Applicant: International Business Machines Corporation, Armonk, NY (US)

(72) Inventors: Eric L. Erpenbach, Oronoco, MN (US); Lakshminarayanan Krishnamurthy, Round Rock, TX (US); Andrew J. Lavery, Austin, TX (US); Richard J. Stevens, Monkton, VT (US); Fernando Jose Suarez Saiz, Armonk, NY (US)

(73) Assignee: International Business Machines Corporation, Armonk, NY (US)

( * ) Notice: Subject to any disclaimer, the term of this patent is extended or adjusted under 35 U.S.C. 154(b) by 330 days.

(21) Appl. No.: 16/047,744

(22) Filed: Jul. 27, 2018

(65) Prior Publication Data

US 2020/0035359 A1    Jan. 30, 2020

(51) Int. Cl.
  *G16H 50/20* (2018.01)
  *G16H 10/60* (2018.01)
  *G16H 50/70* (2018.01)
  *G16H 10/20* (2018.01)

(52) U.S. Cl.
  CPC ............. *G16H 50/20* (2018.01); *G16H 10/60* (2018.01); *G16H 50/70* (2018.01); *G06T 2207/20081* (2013.01); *G16H 10/20* (2018.01)

(58) Field of Classification Search
  CPC ........ G16H 50/20; G16H 50/50; G16H 10/60; G16H 20/00; G16H 50/70; G16H 10/20; G06T 2207/20081; G06Q 50/22–24
  See application file for complete search history.

(56) References Cited

U.S. PATENT DOCUMENTS

| | | | |
|---|---|---|---|
| 6,827,670 B1 * | 12/2004 | Stark | G16H 20/00 482/9 |
| 7,593,952 B2 | 9/2009 | Soll et al. | |
| 8,494,869 B1 | 7/2013 | Frasher et al. | |
| 8,719,051 B2 | 5/2014 | Trifunov et al. | |

(Continued)

OTHER PUBLICATIONS

Anonymous, "Method and System for Managing Cases When an Answer Changes in a Question Answering System" IPCOM000237471D, IP.com, Jun. 18, 2014, 3 pages.

*Primary Examiner* — Robert A Sorey
(74) *Attorney, Agent, or Firm* — Reza Sarbakhsh; Edell, Shapiro & Finnan, LLC

(57) ABSTRACT

According to embodiments of the present invention, medical treatment outcomes are simulated. A system receives a request to determine a medical treatment pertaining to a medical condition of a patient. The request is applied to one or more models, via a processor, to simulate outcomes for a plurality of different medical treatments for the medical condition, wherein the one or more models account for impacts of the plurality of different medical treatments on use of medical treatments awaiting future approval. The medical treatment is determined from the simulated outcomes, via a processor, with a desired level of impact on the medical treatments awaiting future approval based on characteristics of the patient. Methods and computer readable media are also provided herein for simulating medical treatment outcomes.

17 Claims, 6 Drawing Sheets

(56) References Cited

U.S. PATENT DOCUMENTS

| | | | |
|---|---|---|---|
| 2002/0029784 A1* | 3/2002 | Stark | G06F 19/00 128/898 |
| 2012/0047105 A1* | 2/2012 | Saigal | G06F 19/00 706/52 |
| 2013/0024207 A1* | 1/2013 | Anderson | G16H 10/20 705/3 |
| 2013/0124224 A1* | 5/2013 | Srinivasan | G16H 10/60 705/3 |
| 2014/0297311 A1* | 10/2014 | Jackson | G16H 10/60 705/2 |
| 2015/0120319 A1 | 4/2015 | Wilson et al. | |
| 2016/0034457 A1 | 2/2016 | Bradley et al. | |
| 2016/0078182 A1 | 3/2016 | Allen et al. | |
| 2016/0210424 A1 | 7/2016 | Di Battista | |
| 2017/0109390 A1 | 4/2017 | Bradley et al. | |
| 2017/0161446 A1 | 6/2017 | Kronander | |
| 2017/0262614 A1* | 9/2017 | Vishnubhatla | G06Q 50/22 |
| 2017/0372029 A1* | 12/2017 | Saliman | G16H 10/60 |

* cited by examiner

COGNITIVE SYSTEMS FOR GENERATING PROSPECTIVE MEDICAL TREATMENT GUIDANCE

BACKGROUND

1. Technical Field

Present invention embodiments relate to cognitive systems, and more specifically, to cognitive systems for ranking medical treatment options in view of prospective advances in medical technology and optionally patient data.

2. Discussion of the Related Art

Cognitive question and answer (QA) systems are under development in the medical domain to assist physicians with selection of treatment protocols and patient care. Typically, a user asks the QA system a series of medical questions related to a particular patient. In response, the QA system provides best treatment recommendation(s) for a patient based upon existing medical treatments. For example, a specific chemotherapy treatment protocol approved by a governmental regulatory agency may be recommended for a lung cancer patient based upon the patient's medical profile. Similarly, a treatment plan for a diabetic may be recommended based upon existing treatment plans and the patient's medical profile.

In both cases, the results returned by the QA system are retrospective, in that the system only considers treatment options that are available to the patient at the time the medical disorder or disease is discovered. Existing cognitive QA systems are limited to present technologies, e.g., technologies that have been approved by regulatory agencies or therapies that are actively undergoing clinical trials. While such QA systems may provide a ranked list of treatments, in terms of most recommended to least recommended, these cognitive QA systems are limited to available treatments.

SUMMARY

According to embodiments of the present invention, a cognitive medical treatment data processing system is provided comprising at least one processor and at least one memory, wherein the at least one memory comprises instructions executed by the at least one processor to simulate medical treatment outcomes. The system receives a request to determine a medical treatment pertaining to a medical condition of a patient. The request is applied to one or more models, via a processor, to simulate outcomes for a plurality of different medical treatments for the medical condition, wherein the one or more models account for impacts of the plurality of different medical treatments on use of medical treatments awaiting future approval. The medical treatment is determined from the simulated outcomes with a desired level of impact on the medical treatments awaiting future approval based on characteristics of the patient. Methods and computer readable media are also provided herein for simulating medical treatment outcomes.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components. Through the more detailed description of some embodiments of the present disclosure in the accompanying drawings, the above and other features and advantages of the present disclosure will become more apparent.

DETAILED DESCRIPTION

Techniques, systems, and computer readable media are provided to simulate medical treatment outcomes for a patient. In some aspects, a QA medical system may guide a physician and/or patient through currently available treatment options as well as treatment options projected to be available in the future. Current medical treatment cognitive systems do not guide physicians through treatment options with consideration for subsequent treatment choices, e.g., to identify an optimal and non-limiting medical treatment in view of patient data, current medical treatments and future medical treatments.

Present techniques identify a plurality of medical treatments, and for each medical treatment, determine whether contraindications exist for other medical treatments. For instance, if a particular first-line medical treatment has contraindications with other available medical treatments, the system may notify a physician and/or patient of this contraindication. In this case, the physician may select a different first-line treatment (without a contraindication to another medical treatment) so as to optimize future treatment options for the patient.

As medical technology and scientific discoveries evolve, new types of medical treatments become available. While a variety of medical treatments may exist for a particular condition, selecting an optimal treatment remains difficult. For example, while numerous cancer treatments are available, such treatments frequently fail, with patients subsequently undergoing one or more rounds of additional therapy with different medical treatments.

In some cases, the selected first treatment may prevent a physician from subsequently selecting another (second) medical treatment, e.g., due to contraindications of the first treatment with the second treatment. Thus, particular treatment regimens may preclude selection of other currently available treatment regimens as well as treatment regimens that may be available in the future. For example, some patients desiring to enroll in a clinical trial may be unable to do so if they have been previously treated with a therapeutic that may disqualify them from the clinical trial.

For example, an active area of research involves stem cell therapies, in which stem cells may be differentiated into other cells, tissues, or organs, and transplanted into human recipients, or gene replacement therapy in which a corrected gene is delivered to the site of diseased tissue, e.g., via a micro- or nano-liposome, etc., to replace the defective gene in order to restore normal function. While these techniques are limited at present, ongoing research and novel discoveries such as CRISPR-Cas9 technology may allow targeted gene replacement in the future.

Figure 1:
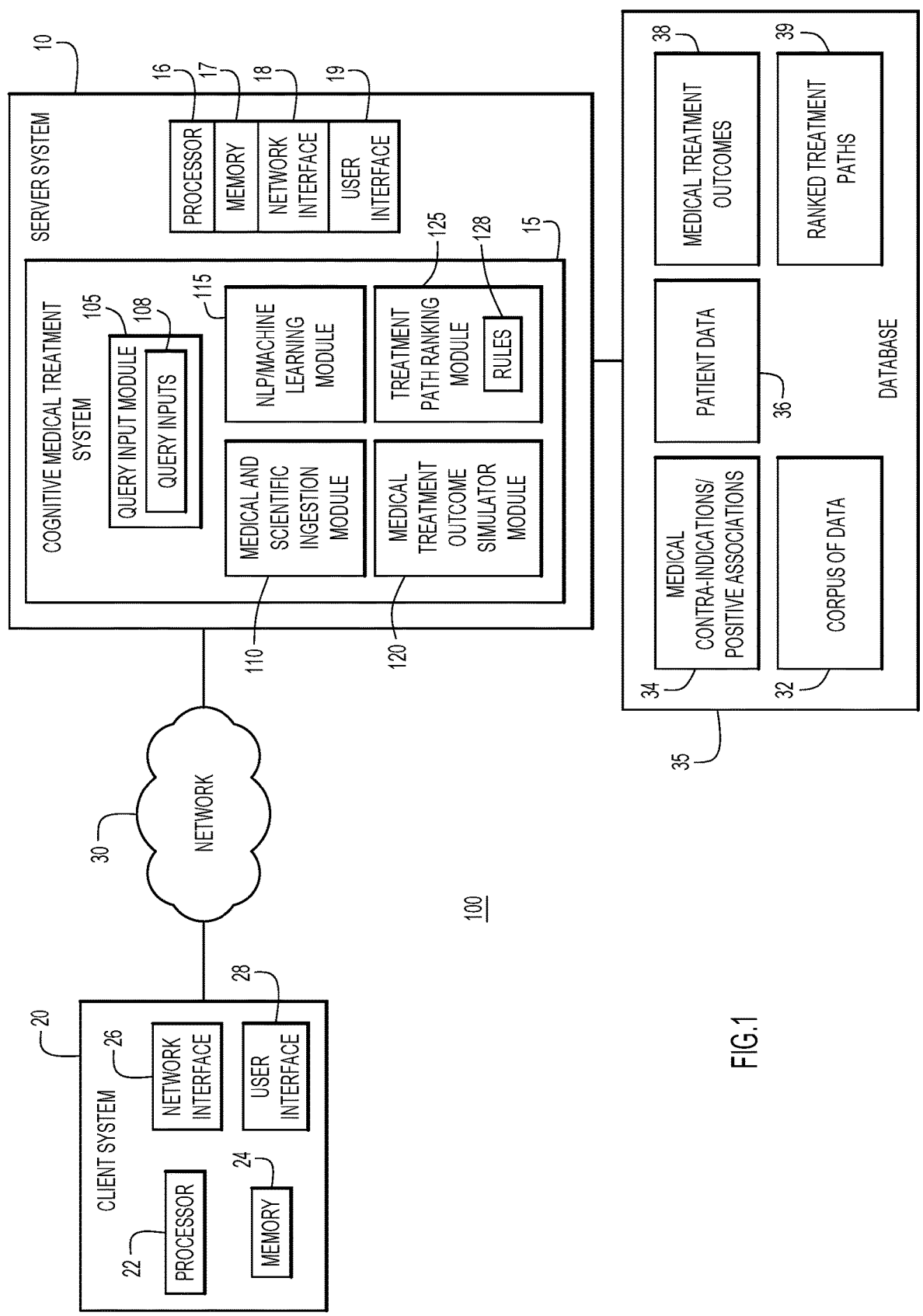
FIG. 1 is a block diagram of an example computing environment for simulating medical treatment outcomes in accordance with embodiments of the present disclosure.

An example environment 100 for use with present invention embodiments is illustrated in FIG. 1. Specifically, the environment includes one or more server system(s) 10, and one or more client or end-user system(s) 20. Server system 10 and client system 20 may be remote from each other and may communicate over a network 30. The network may be implemented by any number of any suitable communications media (e.g., wide area network (WAN), local area network (LAN), Internet, Intranet, etc.). Alternatively, server system 10 and client system 20 may be local to each other, and may communicate via any appropriate local communication medium (e.g., local area network (LAN), hardwire, wireless link, Intranet, etc.).

Client system 20 enables users to submit queries (e.g., queries for medical treatment outcomes, patient data, etc.) to server system 10 to simulate medical outcomes based upon an analysis of a large corpus of data 32 (e.g., scientific data, scientific journals, publically and/or privately accessible chemical databases, databases of known pharmaceutical and/or biologic therapeutic compounds, databases/literature of known genes/DNA, databases/literature of expressed RNA, databases/literature covering proteomics, databases/literature covering metabolomics, clinical trial information, medical information, etc.). Such an analysis may also include consideration of contraindications between various medical treatments.

The server system 10 includes a cognitive medical treatment system 15 to simulate and rank medical treatment outcomes based upon an analysis of the large corpus of data 32, in response to a medical treatment query. A query may be received as query inputs 108. A database system 35 may store various types of information for the analysis as well as any data generated by server system 10 (e.g., corpus of data 32, medical contraindications/positive associations 34, patient data 36, medical treatment outcomes 38, ranked treatment paths 39, etc.). The database system 35 may be implemented by any conventional or other database or storage unit, may be local to or remote from server system 10 and client system 20, and may communicate via any appropriate communication medium (e.g., local area network (LAN), wide area network (WAN), Internet, hardwire, wireless link, Intranet, etc.).

Corpus of data 32 may include any scientific and medical information regarding current and future medical treatment options. Medical contraindications/positive associations 34 may include information regarding conflicts between medical treatment protocols, positive associations between medical treatment options, etc. Patient data 36 may include any information specific to the patient's medical history, demographics, or personal preferences regarding medical treatment. Medical treatment outcomes 38 include the results of the simulations regarding available and future medical treatment outcomes. Ranked treatment paths 39 include ranked decisions trees based on relative or absolute constraints, as provided herein.

Server system 10 and client system 20 may be implemented by any conventional or other computer systems preferably equipped with a display or monitor, a base (e.g., including at least one hardware processor 16, 22 (e.g., microprocessor, controller, central processing unit (CPU), graphical processing unit (GPU), etc.), one or more memories 17, 24 and/or internal or external network interfaces or communications devices 18, 26, (e.g., modem, network cards, etc.) respectfully), along with optional input devices (e.g., a keyboard, mouse or other input device), and any commercially available and custom software (e.g., cognitive medical treatment system 15, server/communications software, browser/interface software, etc.).

Server system 10 comprises cognitive medical treatment system 15, which includes query module 105, medical and scientific ingestion module 110, NLP/machine learning module 115, medical treatment outcome simulator module 120, treatment path ranking module 125, as described herein. In some embodiments, medical treatment outcomes 38, generated by medical treatment outcome simulator module 120, and treatment path 39, generated by treatment path ranking module 125, may be provided to the client system 20 for display to a user. In general, the medical treatment outcomes and/or treatment paths may be ranked or unranked. In some cases, the treatment paths 39 may be provided in a decision tree format.

In other embodiments, a graphical representation of the medical treatment outcomes 38 or the treatment paths 39 may be provided to the user in any suitable format (e.g., a network of linked nodes, a list, a table, a knowledge graph, etc.). Client system 20 may present a graphical user (e.g., GUI, etc.) or other cognitive medical treatment system interface 15 (e.g., command line prompts, menu screens, etc.) to solicit information from users pertaining to the desired analysis, and may provide reports (e.g., lists, spreadsheets, graphical results, etc.) including results, which may include medical treatment outcomes 38 and treatment paths 39 (e.g., ranked based upon user preferences, ranked to preserve future medical treatment options, or a combination thereof, etc.).

Alternatively, one or more client systems 20 may analyze a corpus of documents to generate treatment outcomes 38 and/or treatment paths 39 (e.g., ranked based upon user preferences, ranked to preserve future medical treatment options, or a combination thereof, etc.) when operating as a stand-alone unit. In a stand-alone mode of operation, the client system stores or has access to the data (e.g., database 35, including corpus of data 32, medical contradictions/positive associations 34 (information that may be extracted from the corpus of data 32 and/or manually provided), patient data 36 (information containing patient demographics, medical history, or preferences, etc.)) analyzed by cognitive medical treatment system to generate medical treatment outcomes 38 and treatment paths 39. The graphical user (e.g., GUI, etc.) or other interface 28 (e.g., command line prompts, menu screens, etc.) solicits information from a corresponding user pertaining to the desired documents and analysis for input into the cognitive medical treatment system 15 and may provide reports (medical outcomes 36, treatment paths 39, etc.) to the user.

Cognitive medical treatment system 15 may include one or more modules or units to perform the various functions of present invention embodiments described herein. The various modules (e.g., query input module 105, medical and scientific ingestion module 110, NLP/machine learning module 115, medical treatment outcome simulator module 120, treatment path ranking module 125, etc.) may be implemented by any combination of any quantity of software and/or hardware modules or units, and may reside within memory 17 of the server for execution by processor 16.

In some aspects, query inputs 108 may include query terms provided by the user via user interface 28. The query terms 108 may include medical conditions for which medical treatment outcomes are sought. In some aspects, the user may customize the query, e.g., entering options or patient preferences or by accessing stored patient data 36, to constrain the medical treatment outcomes 38 and treatment paths 39. For example, if a user does not want to include a particular type of treatment (e.g., does not want to undergo radiation therapy, wishes to avoid a surgical procedure, etc.), or has a preexisting medical condition which would preclude a specific type of treatment (e.g., an allergy to a specific medication, or an adverse reaction with another medication previously prescribed to the patient, etc.), this information may be provided as part of the query input, specified in patient data 36, or applied as a relative constraint.

Medical and scientific ingestion module 110 may parse corpus of data 32, which may include spreadsheets, tables, lists, unformatted text, formatted text, structured data, etc. for scientific and medical data. In some embodiments, the data may be present in image format, and optical character recognition may be performed to convert the image into a text rendered format.

Medical and scientific information ingestion module 110 considers information and evidence about available treatments as well as future treatments that are not currently available as well as academic research that may lead to novel types of future treatments. The ingestion module 110 monitors future options that may apply to a patient, so that any changes in simulated medical treatment outcomes (e.g., availability of a new treatment) are provided to the doctor and/or patient.

NLP/Machine learning module 115 may utilize natural language processing (NLP) and/or machine learning to extract entities relating to medical treatments, associated outcomes and contraindications between medical treatments from the corpus of data 32. In some cases, a document may be analyzed to extract medical conditions and associated treatments. In some cases, the context of the entity within the document can be semantically analyzed, e.g., by decomposing words and/or phrases (e.g., into nouns, verbs, objects, adjectives, adverbs, etc.) into terms used in the local or global vicinity of the entity to establish context of the entity as well as positive associations and contraindications.

The medical conditions may be predefined from a list and/or module 115 may identify medical conditions through NLP processing and/or machine learning. For example, if hearing loss is provided as a medical condition, module 110 may also identify hearing loss in other contexts including deafness, partial deafness, reduced hearing, hearing reduction, etc.

Once the medical conditions are identified, the context of the medical conditions within the documents may be evaluated, and relationships may be determined and stored as medical contraindications/positive associations 34. For example, hearing loss (including associated synonyms) may be identified as a medical condition by a user or by the system 15. The system 15 may identify treatments for hearing loss, including but not limited to surgery, medical devices (cochlear implants), and gene therapy or transplantation. Module 115 may additionally identify one or more phrases indicating that cochlear implants destroy hair cells, and that some treatments for hearing loss, gene therapy, may restore function of hair cells. Gene therapy may involve transferring corrected DNA encoding functional proteins into hair cells, thereby restoring the function of the hair cells by expression of the functional protein. Based on this information, the system may determine that a contraindication exists between cochlear implants and hair cells. Since cochlear implants involve a surgical procedure that destroys hair cells that stimulate the auditory nerve, subsequent treatments with gene therapy is not an option, and therefore, cochlear implants are contraindicated for patients for which gene therapy may be a future medical treatment option. Similarly, other treatments for hearing loss may be extracted, and terms and/or phrases may be identified which describe the treatment, e.g., including side effects, physiological effects, etc., to establish other contraindications.

In some cases, the NLP/machine learning module 115 may identify treatments that are associated with a physiological change, such as removal or destruction of cells, tissues, or organs due to surgical intervention, or therapies that alter cell, tissue, or organ function, etc. These treatments may be automatically identified as limiting treatments, without specific knowledge of a future therapeutic option that would be precluded by these treatments.

Thus, for each disorder, a series of records may be established containing information about the medical condition, available and potential future treatments, contraindications between treatments and/or future treatments, positive associations between treatments and/or future treatments. In some cases, the series of records may be reviewed for accuracy, in its entirety or a portion thereof.

NLP/machine learning module 115 may analyze data (e.g., patient data, medical and scientific publications, clinical trial information, 'omic' data, etc.) to identify contraindications (as well as positive correlations) of a first treatment relative to a second treatment. In some aspects, contraindications are used to generate absolute constraints. Relative constraints apply to specific patients, and may be derived based upon patient data (e.g., a patient's age, desire to avoid certain types of treatment, or pre-existing conditions) or may be provided as input to the system as patient data 36.

Medical treatment outcome simulator module 120 may analyze the information provided by module 110 and 115 to simulate medical treatment outcomes. In some cases, the medical treatment outcomes may be provided in the form of a list or table, while in other cases, decision trees may be constructed pertaining to medical treatment outcomes. In some cases, a treatment may correspond to a particular therapeutic, in other cases, a treatment may correspond to a combination of therapeutics.

For example, a first level of a decision tree may contain cochlear implants as a treatment. Any subsequent treatments which affect hair cells are omitted from this decision tree. The omitted treatment may be displayed, so that the user is aware of tradeoffs. In some cases, the user may enter or select treatments to omit so that such outcomes will not be represented in the decision tree. Thus, the decision tree may be customized to particular patients. While this example involves the use of decision trees, the data may be presented in any suitable format, including but not limited to, e.g., lists, tables, linked nodes, etc. Module 120 may simulate likely outcomes of treatments, and the subsequent treatment options based on those outcomes.

In some aspects, medical treatment outcome simulator module 120 may comprise one or more models to simulate available and future medical treatment outcomes for a plurality of different medical conditions. The models may account for the impact of an available medical treatment on subsequent use of a future medical treatment. In some cases, the simulator may provide an estimate of when the future medical treatment may be available. For example, new therapies frequently progress through a defined series of stages, e.g., pre-clinical development; first, second and third phases of clinical trials; regulatory review and approval, which may be associated with certain lengths of time, e.g., an average length of time to complete a first, second or third stage of a clinical trial, etc. In other cases, certain future therapies may be approved for certain demographics, e.g., adults, infants/children, etc. Some therapies have only been approved for use in adult or pediatric populations. Such estimates may be updated as phases of clinical trials, approvals, etc. are completed. In general, the simulator may consider various factors including but not limited to target patient populations, projected time to availability, projected cost, positive associations between medical treatments (e.g., to optimize therapies), contraindications between available and future treatments, success rates/efficacy, duration of treatment, etc. These factors may be considered by treatment path ranking module 125, in order to determine a suitable treatment or a treatment path for an individual based on patient data that defines characteristics (e.g., age, medical history, preferences, etc.) of the patient.

In some cases, a medical treatment may include a plurality of stages, and at each stage of the medical treatment, modeling may be performed to produce simulated outcomes for that stage of medical treatment. Thus, a plurality of different medical treatments may include a plurality of stages, and medical treatment options may be modeled at each stage of a medical treatment to produce simulated outcomes for that medical treatment.

Once the various medical treatment outcomes have been simulated, the outcomes and/or treatment paths may be ranked using treatment path ranking module 125. For example, in some cases, medical treatment outcomes and/or pathways with the fewest limitations or contraindications may be ranked highest. In other cases, the results may be ranked according to associated patient profiles. For example, treatment outcomes/paths may be prioritized based on gender, age, patient preferences, pre-existing conditions, etc. or any other custom input provided by the user. Patient data may also comprise information regarding the context of the patient, e.g., age, preferences, socio-economic factors, etc., which may be used in determining an optimal treatment path for the patient. For example, in some cases, patients may wish to avoid certain side effects of treatments, such as hair loss, etc., and may specify this information in patient data 36. In other cases, patients may specify a given period of time in which they are able to wait for a new treatment to become available. Treatment path ranking module 125 provides the best overall treatment path(s) considering all simulated scenarios for the treatment paths, in view of patient data, and the treatment options available at each stage along the treatment path. Rules for ranking treatment options and decision trees may be stored as rules 128.

Treatment path ranking module 125 considers various characteristics of the patient when ranking various treatments and treatment paths, to determine a suitable treatment/treatment path for the patient based on patient data that provides characteristics (e.g., age, medical history, preferences, etc.) of the patient. Thus, patient data may be used to identify possible treatments/treatment paths which are most suited (e.g., as designated by a high ranking) to a specific patient.

Figure 2A:
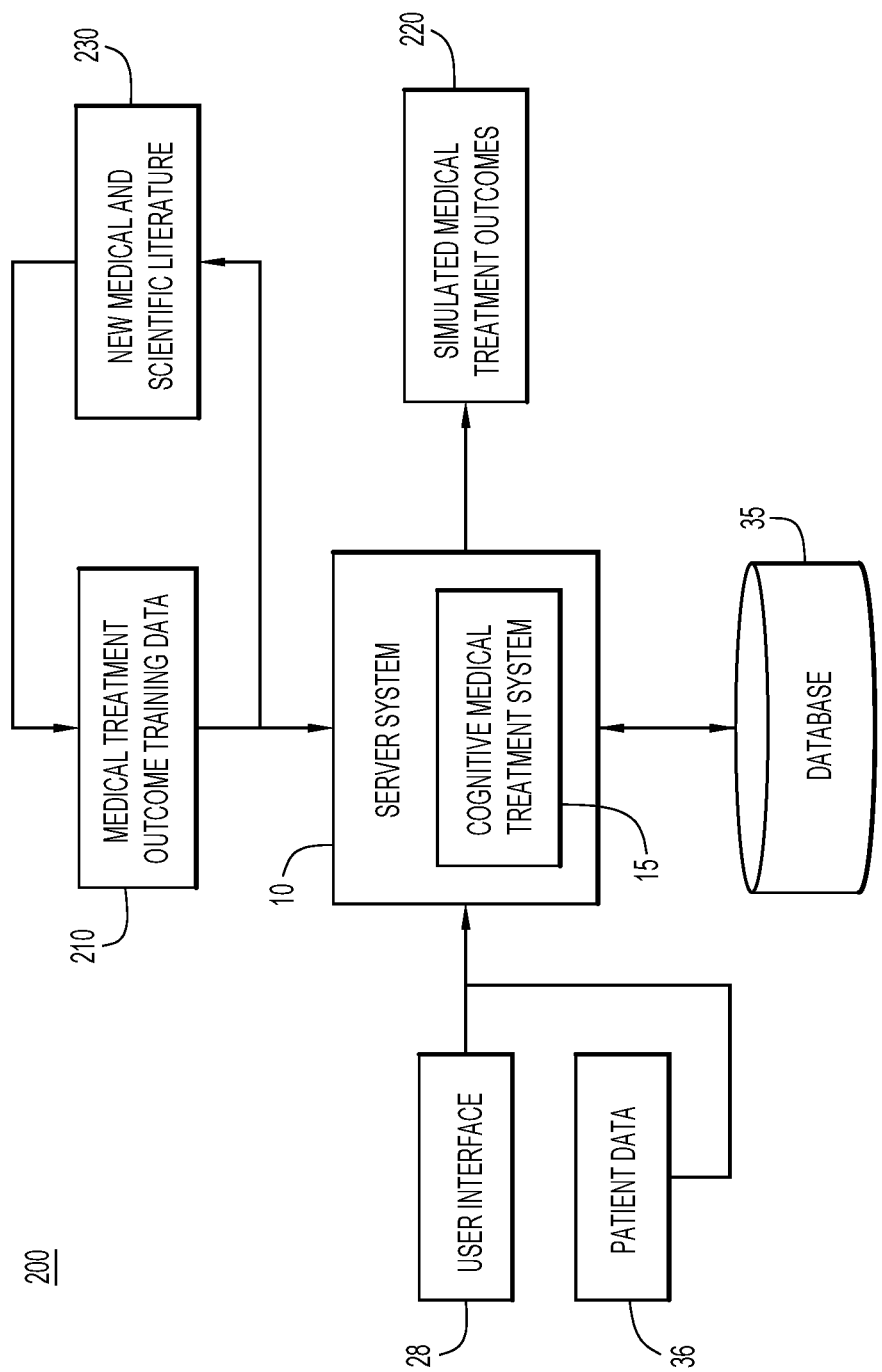
FIGS. 2A-2B are an example illustration and a high level flow chart of operations for training a medical treatment outcome system, according to embodiments of the present disclosure.

FIG. 2A shows an illustration of a computing environment 200 showing training of the cognitive medical treatment system 15. The cognitive medical treatment system 15 may comprise medical and scientific ingestion module 110, NLP/machine learning module 115, medical treatment outcome simulator module 120, and treatment path ranking module 125 and may access database 35. The system may receive input and visualize results through user interface 28.

Medical treatment outcome training data 210, which may include available and future treatments, may be provided to cognitive medical treatment system 15 to train the system and generate in response to a query via user interface 28 (and optionally, user provided patient data 36) simulated medical treatment outcomes 220, which may include medical treatment paths (e.g., decisions trees). The system 15 may ingest new medical and scientific literature 230, e.g., on a periodic basis, as such information becomes available, and this information may be added to the training data set in order to train the system on additional or new information and/or treatments that become available, to generate up-to-date simulated medical treatment output options 220.

Figure 2B:
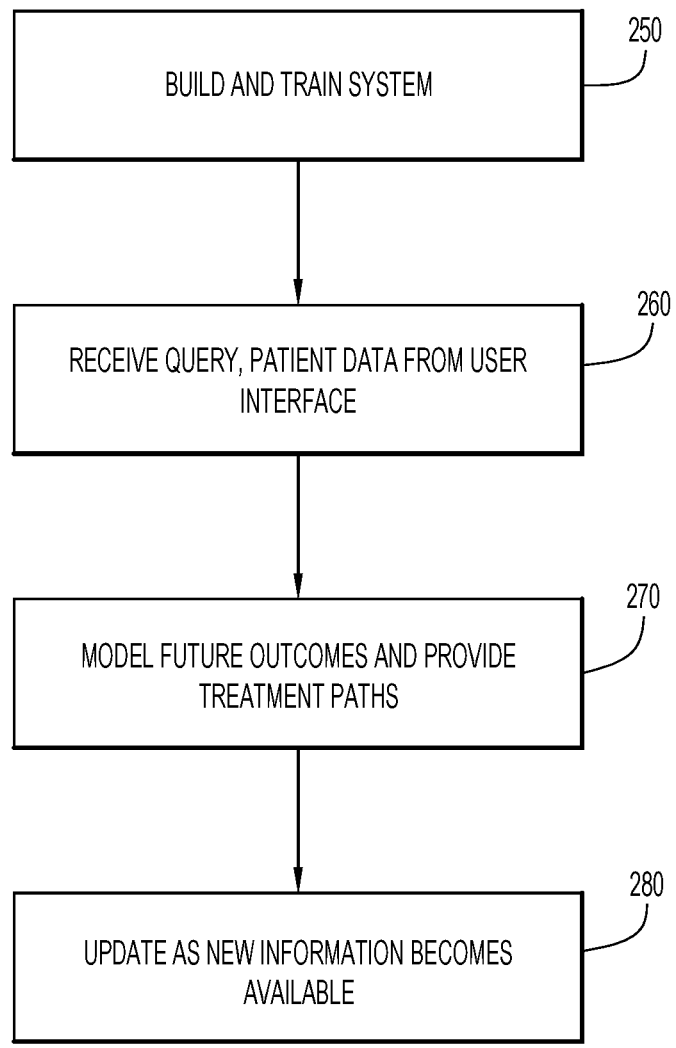

FIG. 2B shows a flow chart corresponding to the operations of FIG. 2A. At operation 250, the system 15 is built and trained using training data 210. At operation 260, the system may receive a query and optionally patient data expressing patient preferences, medical condition of patient, age of patient, etc. For example, the system may receive a query in the form of a question or any other suitable input format, such as "What are the best treatment options for a lung cancer patient that is 40 years old?" At operation 270, the system simulates medical treatment outcomes (including future and available outcomes) to provide treatment paths, which may be ranked based on patient data or other preferences of the patient. The decision tree also may include potential future treatment options, which are not yet available at the time of simulation. The system provides the simulated medical treatment outcomes (as individual outcomes or as treatment paths), which may be ranked, along with supporting evidence for the provided options. Thus, the system may provide real world evidence, e.g., information from the corpus of data including clinical trials or scientific literature, which supports the treatment paths.

In some aspects, the system may be provided with a training data set 210, with which to learn and apply rules for extracting medical treatment outcomes and identifying relationships (positive associations and contraindications) between different medical treatment outcomes. In some aspects, these relationships may be reviewed by a curator for accuracy. In other cases, additional training data may be provided to reduce errors.

At operation 280, the system may monitor treatment paths as treatment options change, so that the physician and/or patient may be made aware of new medical treatment options in a treatment path that are available (e.g., granted regulatory approval). Operations 250-270 may be repeated, as the system ingests new data to train on new treatment options. Previously generated treatment paths may be updated, as future medical treatment options under consideration by a doctor and/or patient have a change in status to become available medical treatment options.

Figure 3:
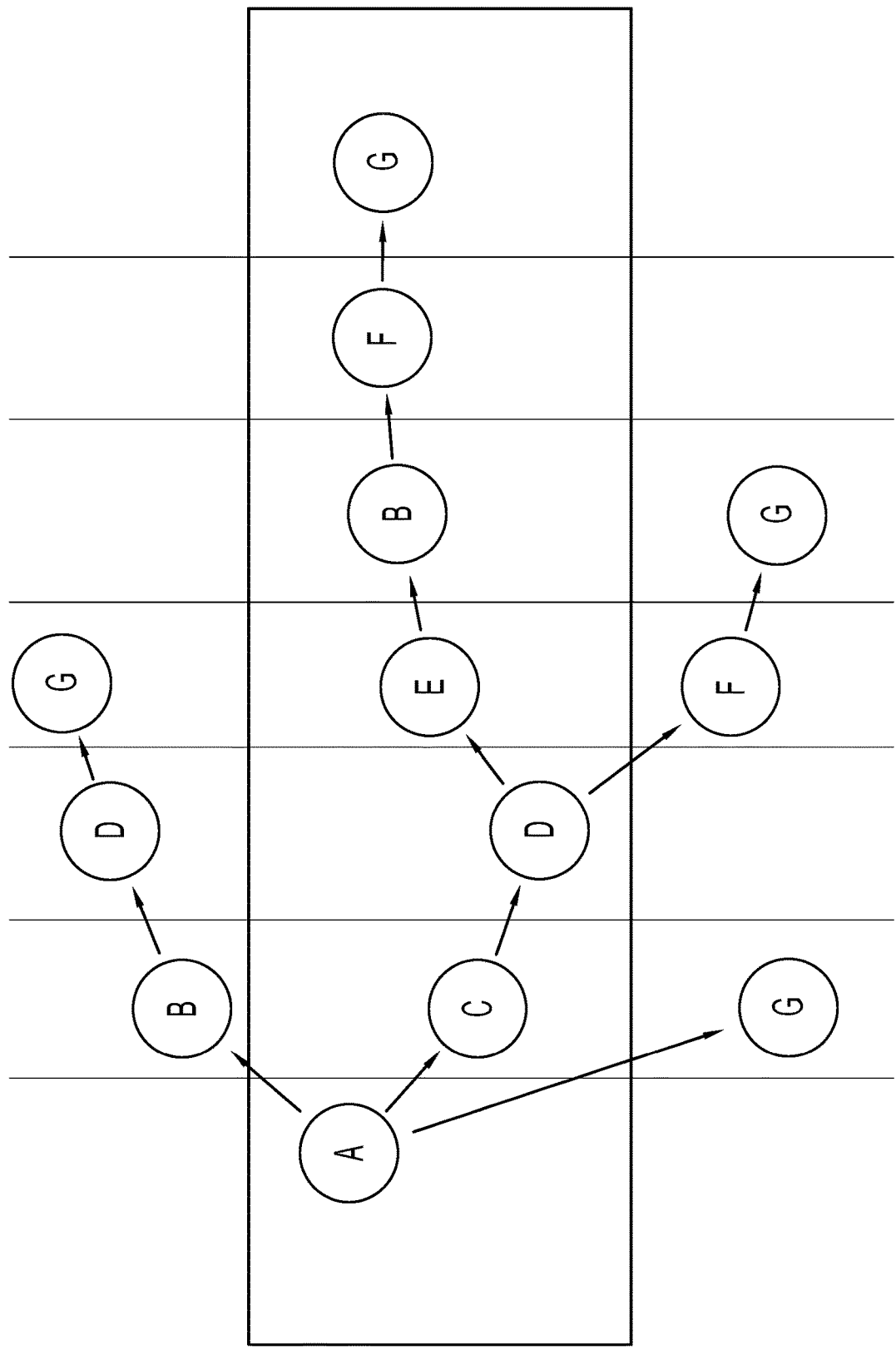
FIG. 3 is an illustration showing a portion of medical outcomes represented as a decision tree, in accordance with embodiments of the present disclosure.

FIG. 3 shows an example of a portion of a treatment decision tree. While evaluating options, the system may model or simulate medical treatment outcomes for each treatment. For a given set of treatments, the outcomes may be evaluated for each treatment, taking into account relative rules (e.g., generated from patient data and/or preferences) and absolute rules. Based on those outcomes, the next steps for treatment are evaluated. Thus, the simulations may consider rules for all patients and/or rules pertaining only to a particular patient's situation.

In this example, a first treatment 'A' is selected. At the second level of treatment, treatment options 'B' and 'C' and 'G' are selected. At the third level of treatment, treatment option 'D' is provided, and so forth. Here, the rules generate a decision tree showing that treatment option 'G' precludes all future treatments. Additionally, treatment 'B' only precludes later treatment with 'C'. Thus, the path enclosed in a rectangle preserves all future treatment options and may be suitable for a subset of young patients. Other pathways may be more suitable for older patients, or for patients with other preferences.

As an example, there may be two choices of first-line chemotherapy for a patient. The first chemotherapy option may have associated side effects (e.g., raising blood pressure, altering kidney or liver or immune function (e.g., as detected by blood testing), increase risk for developing cardiac disease, or some other side effect) with a success rate of 25%. On the other hand, the second chemotherapy option may have fewer or no side effects, with a success rate of 15%. In this case, selection of the first chemotherapy option may be associated with side effects that may preclude a patient from enrolling in an upcoming clinical trial, as such trials may seek to enroll patients without complicated health histories, in order to better assess the impact of the experimental therapy. For example, a patient with pre-existing cardiovascular disease may not be selected for a clinical trial, wherein a goal of the clinical trial is to ascertain whether the experimental therapy is associated with an increased risk of developing cardiac disease.

The system may determine through this simulation that of the two choices, the first treatment path may result in restricted choices for future medical treatment options, and therefore, the best overall treatment path may be the second chemotherapeutic treatment. Other factors may be included in this analysis through establishing rules, such as treatment efficacy. If two treatments have similar efficacies, the treatment with fewer side effects may be selected. As another example, if a first treatment has high efficacy but with potential side effects that would limit future treatment options, and a second treatment has low efficacy relative to the first treatment option, then the system may prioritize the treatments based on age, e.g., recommending the second treatment option for a patient having an age of 25 and the first treatment option for a patient having an age of 70.

As another example, a patient may have hearing loss. If the patient has had sudden profound hearing loss in both ears, and the patient currently has no hearing, then a simulated medical treatment outcome of waiting ten years for a treatment will be ranked low among the treatment paths as the patient needs a more immediate solution. In this case, a cochlear implant in at least one ear may be recommended. On the other hand, if the patient is a ten year old with profound hearing loss in one ear and 100% hearing in the other ear, the system may not recommend a cochlear implant. In this case, the patient's outcome with a hearing aid may suffice, considering perfect hearing in the other ear, and this treatment option will allow for future research and technology to be used without destroying such options with a cochlear implant.

As yet another example, a diabetes patient may be evaluated for treatment options. A drug may be in clinical trials that would be suitable for the patient, but is awaiting regulatory approval. Based on clinical trial results and similarity of the patient to the type of patients in the clinical trial, the system may predict that the patient would benefit from this treatment. However, the future drug may have conflicts or deleterious side effects with other available treatments, and therefore, the future treatment may be not be allowed if the patient has been on a conflicting treatment. Thus, other options may be selected, allowing future options to be conserved. Present techniques may guide the physician and patient to identify ideal treatment choices today, with an outlook as to what treatments may be available in the future.

Thus, in the case of the diabetes patient, the doctor and patient may treat diabetes with a particular drug today, and may await approval of a specific new drug (future treatment), or any other suitable option to become available. The doctor and/or patient may be made aware of changes as drugs and/or treatment are approved, in order to make informed decisions based on up-to-date information.

Figure 4:
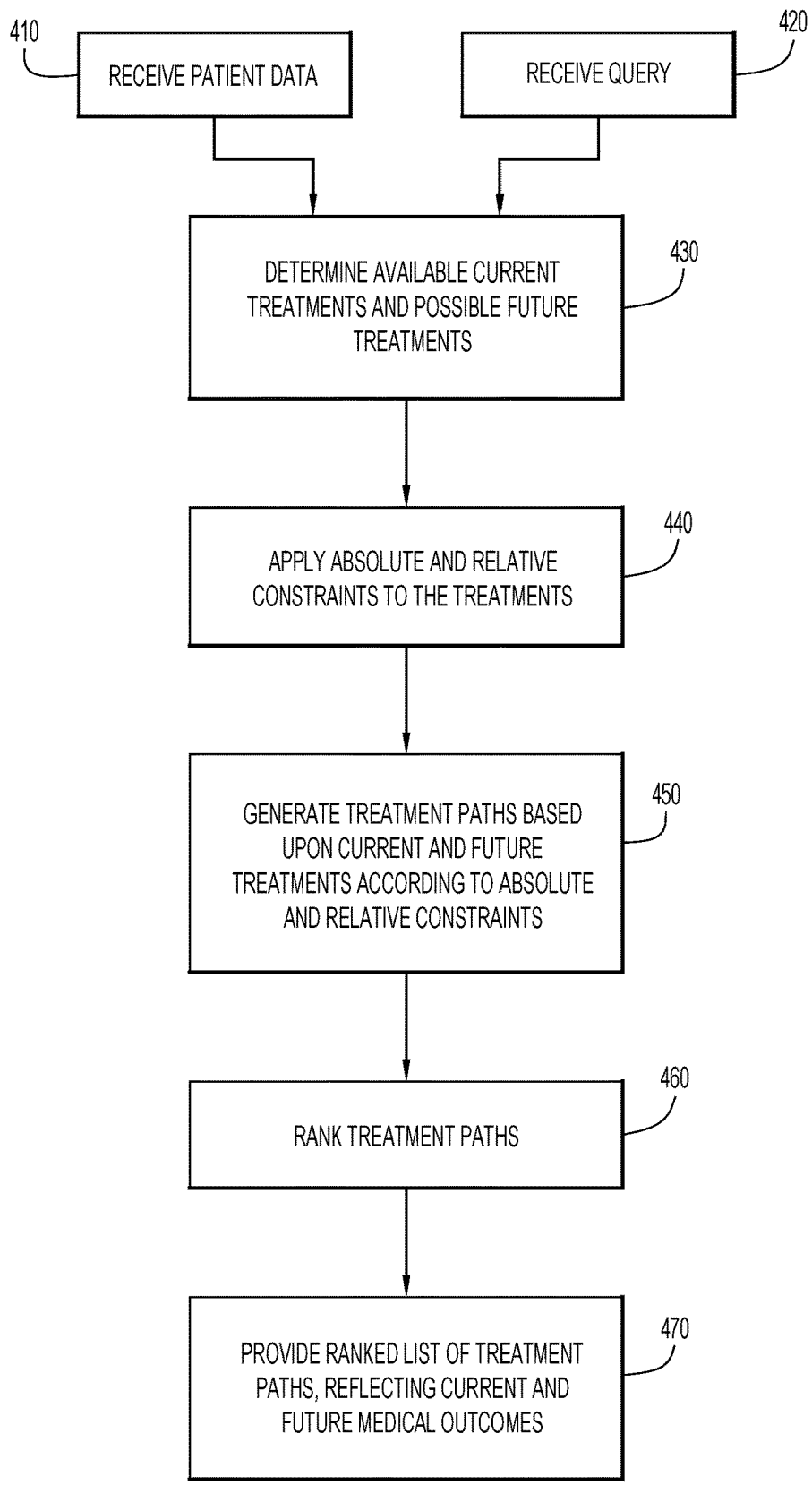
FIG. 4 is a detailed flowchart of operations for simulating medical treatment outcomes, according to embodiments of the present disclosure.

FIG. 4 shows a process which includes evaluation of absolute and relative constraints on medical treatments. Those constraints may be either "absolute" constraints or "relative" constraints. An absolute constraint may be a rule applied to all patients, such as "If a patient has received previous treatment with drug X, the patient cannot receive repeat treatment with the same drug due to drug exposure limits." Therefore, when evaluating treatment paths, if an absolute constraint is detected, then future medical treatments will be restricted as governed by the corresponding rule. As another example, some clinical trials seek to enroll patients that have not been exposed to specific available medical treatments. Thus, treatment by certain therapies may disqualify a patient from an ongoing or future clinical trial.

A relative constraint may be a rule based on a preference of the patient, patient data, or other medical information pertaining to the patient. For instance, a patient may not wish to wait a long period of time for a future treatment to become available, and this preference may be reflected in the patient data, e.g., by setting a time limit in which the patient is willing to wait for a new treatment option. As another example, financial aspects of treatment may be a constraint, and depending on the patient's insurance or financial resources, certain treatments may be limited. Treatment A may lead to a treatment path that is estimated to cost an average of $500 per month for the rest of the patient's life and may have an outcome of 80% success. Treatment B may have a predicted cost of $100 per month, and may have an outcome of 75% success. While both medical treatments may be possible in the treatment path, depending on insurance or financial resources, the less expensive option may be preferable.

Referring again to FIG. 4, a more detailed flowchart of generating a ranked list of treatment paths using relative and absolute constraints are provided, according to the techniques provided herein. At operations 410 and 420, patient data and a query is received. At operation 430, available current treatments and possible future treatments are determined. At operation 440, absolute and relative constraints are applied to the current treatments and the possible future treatments. At operation 450, treatment paths are generated based upon current and future treatments according to absolute and relative constraints. At operation 460, treatment paths are ranked. At operation 470, a ranked list of treatment paths are generated, reflecting current and future medical outcomes.

Figure 5:
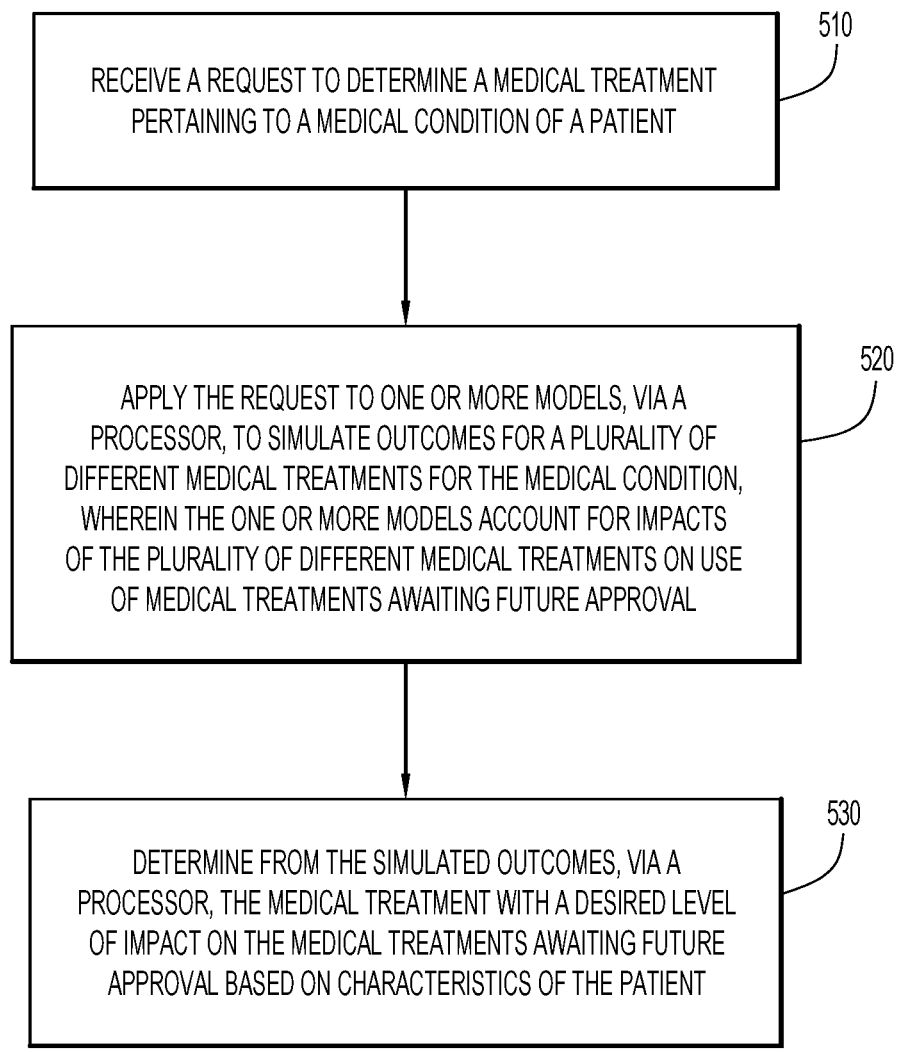
FIG. 5 is a high level flowchart of operations for simulating medical treatment outcomes, according to embodiments of the present disclosure.

FIG. 5 shows a flowchart of operations for modeling future treatment options, according to embodiments of the present disclosure. At operation 510, a request is received to determine a medical treatment pertaining to a medical condition of a patient. At operation 520, the request may be applied to one or more models, via a processor, to simulate outcomes for a plurality of different medical treatments for the medical condition, wherein the one or more models account for impacts of the plurality of different medical treatments on use of medical treatments awaiting future approval. At operation 530, the medical treatment is determined from the simulated outcomes, via a processor, with a desired level of impact on the medical treatments awaiting future approval based on characteristics of the patient.

According to aspects of the invention, a QA medical system may receive patient data and a query to provide a ranked list of treatment options in order to guide a physician and/or patient through the process of selecting an optimal treatment in view of the patient data, current medical treatments, and possible future treatments. The system simulates likely outcomes of treatment options, and the subsequent treatment choices based on those outcomes. The best overall treatment path(s) that consider all simulated scenarios for the treatment paths are provided, along with the medical treatments available at each stage along the treatment path. In some aspects, information and evidence about promising treatments and research that may not apply or be available to a patient today, may be a preferable treatment option in the future. The system may monitor future medical treatments that may apply to the patient and may update treatment decision trees to incorporate changes in simulated future treatment outcomes as such treatments become available. The updated future medical treatment decision trees may be provided to the physician and/or patient.

For example, in some cases, the system may determine that a less than optimal first-line treatment combined with an optimal second-line treatment provides a better outcome than an optimal first-line treatment that precludes a second line treatment. Thus, the system seeks to optimize sequences of treatments, based on the corpus of data (e.g., including medical and scientific literature, early and late phase clinical trials, patient preferences, etc.) to determine the optimal treatment path for a patient in a non-limiting manner, such that preclusion of future treatments is minimized.

The simulated treatment system, unlike other applications based solely on retrospective analysis of prior patient cases, is prospective, analyzing current and future medical treatments that may be affected by selection of available current treatments. An advantage of a prospective approach is considering, in an unbiased way, both the best choice(s) of treatment available today, but also, the best choice(s) of emerging new treatments, which are not available today but are showing promise in early research and/or clinical trials. In rapidly evolving fields like oncology, considering new emerging treatments that typically yield much better results than available treatments is one of the differentiators between the present application and other approaches.

Present embodiments offer significant improvements over traditional approaches. Traditional approaches may select a treatment which may later preclude treatment of a superior treatment option. Present invention embodiments bypass this inefficiency, allowing instead for an optimal medical treatment decision path to be selected, along with automated monitoring of new treatments as such treatments become available.

Accordingly, present invention embodiments may be used as part of a predictive analytics system and/or methodology to generate predictions based upon the analysis of a corpus of information including both entities and non-entities. Present invention embodiments also allow for both entities and non-entities to be searched across a corpus of data. Accordingly, entity to entity relationships, entity to non-entity relationships, and non-entity to non-entity relationships may each be considered when making inferences and predictions on information from processing millions or tens of millions of documents. These techniques allow novel relationships to be discovered from searching complex feature spaces that are not otherwise evident. Additionally, such novel relationships may be discovered, in real time or near real time, as inputs may be changed and adjusted in real time to tailor search results to particular queries.

The embodiments provided herein allow for future medical treatments (predictions) to be considered in order to provide a more complete and robust predictive analytics capability using both available and future treatments. As future treatments become available, the models may be updated to reflect available treatments, in order to continually improve and refine such models.

The embodiments provided herein may be applied to the field of medical diagnostics, to insurance companies to model future medical costs, and so forth. It will be appreciated that the embodiments described above and illustrated in the drawings represent only a few of the many ways of modeling treatment paths for current and future medical treatments. It will also be appreciated that the methods provided herein may be implemented by a computer as part of a cognitive system.

In some aspects, the system may dynamically determine changes in decision trees. For example, a new treatment may become available, and the system may automatically update the models and perform another simulation to regenerate decision trees in view of the new information. In some cases, the decision trees may change, e.g., in cases in which the new treatment meets absolute and relative constraints and is incorporated into the decision tree. The system may automatically send a notification to the physician and/or patient, indicating that the treatment path has changed, and that new treatment options are available.

In some cases, the decision trees may be used to track administration of treatments. As an example, for a patient that has selected a particular treatment path from a decision tree, the system may be used to track and monitor patient progress through the treatment path. For each stage of a treatment, or for each treatment in a treatment path, the system may send notifications regarding subsequent stages or treatments to ensure that the patient adheres to their selected plan. For stages or treatments that involve collection of patient medical data, the system may send reminders to update the patient data in the system. In some cases, the system may regenerate treatment outcomes and decision trees based on updated patient medical information, to provide up-to-date results.

In some cases, the treatment may be adjusted, e.g., by the system or by a user. For example, a user may modify the treatment or treatment paths based on changes in user preference. As another example, if a treatment comprises multiple stages, and the simulated results for a particular stage do not match a patient's outcome at that particular stage, the system may reconfigure the decision tree and treatment paths to select or prioritize a different treatment. Similarly, for a treatment path comprising multiple treatments, if the simulated results for a particular treatment do not match the patient's outcome at that particular level of the path, the system may reconfigure the decision tree to select or prioritize a different treatment path.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, cognitive system 15, user interface 28, etc.). These systems may include any types of monitors and input devices (e.g., keyboard, mouse, voice recognition, etc.) to enter and/or view information.

It is to be understood that the software (e.g., cognitive system 15, user interface 28, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., cognitive system 15, user interface 28, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., corpus of data 32, medical contraindications and positive associations/positive associations 34, patient data 36, medical treatment outcomes 38, treatment paths 39, and any other information including query inputs 108, rules 128, etc.). The database system may be implemented by any number of any conventional or other databases, data stores or storage structures (e.g., files, databases, data structures, data or other repositories, etc.) to store information (e.g., corpus of data 32, medical contraindications and positive associations/positive associations 34, patient data 36, medical treatment outcomes 38, treatment paths 39, and any other information including query inputs 108, rules 128, etc.). The database system may be included within or coupled to the server and/or client systems. The database systems and/or storage structures may be remote from or local to the computer or other processing systems, and may store any desired data (e.g., corpus of data 32, medical contraindications/positive associations 34, patient data 36, medical treatment outcomes 38, treatment paths 39, and any other information including query inputs 108, rules 128, etc.).

The present invention embodiments may employ any number of any type of user interface (e.g., Graphical User Interface (GUI), command-line, prompt, etc.) for obtaining or providing information (e.g., corpus of data 32, medical contraindications/positive associations 34, patient data 36, medical treatment outcomes 38, treatment paths 39, and any other information including query inputs 108, rules 128, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The results may include any information arranged in any fashion, and may be configurable based on rules or other criteria to provide desired information to a user (e.g., corpus of data 32, medical contraindications/positive associations 34, patient data 36, medical treatment outcomes 38, treatment paths 39, and any other information including query inputs 108, rules 128, etc.).

The present invention embodiments are not limited to the specific tasks or algorithms described above, but may be utilized for any system in which consideration of available and future medical treatments are desired.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method, in a cognitive data processing system comprising at least one processor and at least one memory, the at least one memory comprising instructions executed by the at least one processor to cause the at least one processor to simulate medical treatment outcomes, the method comprising:
   receiving a request to determine a medical treatment pertaining to a medical condition of a patient;
   applying the request to one or more machine learning models, via a processor, to simulate outcomes for a plurality of different medical treatments for the medical condition, wherein the one or more machine learning models account for impacts of the plurality of different medical treatments on use of medical treatments awaiting future approval, wherein the one or more machine learning models are trained based on data including outcomes of newly available medical treatments and outcomes of new medical treatments awaiting future approval, and wherein accounting, by the one or more machine learning models, for the use of medical treatments awaiting for future approval includes determining whether applying the different medical treatment to the patient precludes the patient from later receiving the medical treatments awaiting future approval; and
   determining, via a processor, the medical treatment from the simulated outcomes based on a level of impact on the medical treatments awaiting future approval from applying the medical treatment to the patient, wherein the level of impact is based on characteristics of the patient.

2. The method of claim 1, wherein determining the medical treatment further comprises:
   ranking a plurality of medical treatments for the request based on the simulated outcomes.

3. The method of claim 1, wherein the one or more models employ a plurality of constraints for the plurality of different medical treatments, wherein the plurality of constraints includes an absolute constraint applied to all patients and a relative constraint that is applied based on the characteristics of patients.

4. The method of claim 1, wherein the plurality of different medical treatments includes a plurality of stages, and the applying the request to one or more models further comprises:
   modeling medical treatment options at each stage of a medical treatment to produce simulated outcomes for that medical treatment.

5. The method of claim 1, wherein a plurality of medical treatments is arranged in a decision tree to optimize medical treatment options for both available and future medical treatments.

6. The method of claim 5, wherein a decision tree having an arrangement of medical treatments that preclude use of a future medical treatment is ranked lower than a decision tree having an arrangement that does not preclude the use of a future medical treatment.

7. A system for simulating medical treatment outcomes comprising at least one processor configured to:
   receive a request to determine a medical treatment pertaining to a medical condition of a patient;
   apply the request to one or more machine learning models to simulate outcomes for a plurality of different medical treatments for the medical condition, wherein the one or more machine learning models account for impacts of the plurality of different medical treatments on use of medical treatments awaiting future approval, wherein the one or more machine learning models are trained based on data including outcomes of newly available medical treatments and outcomes of new medical treatments awaiting future approval, and wherein accounting, by the one or more machine learning models, for the use of medical treatments awaiting for future approval includes determining whether applying the different medical treatment to the patient precludes the patient from later receiving the medical treatments awaiting future approval; and
   determine the medical treatment from the simulated outcomes based on a level of impact on the medical treatments awaiting future approval from applying the medical treatment to the patient, wherein the level of impact is based on characteristics of the patient.

8. The system of claim 7, wherein the at least one processor is further configured to rank a plurality of medical treatments for the request based on the simulated outcomes.

9. The system of claim 7, wherein the one or more models employ a plurality of constraints for the plurality of different medical treatments, wherein the plurality of constraints includes an absolute constraint applied to all patients and a relative constraint that is applied based on the characteristics of patients.

10. The system of claim 7, wherein the plurality of different medical treatments includes a plurality of stages, and wherein the at least one processor is further configured to:
    model medical treatment options at each stage of a medical treatment to produce simulated outcomes for that medical treatment.

11. The system of claim 7, wherein a plurality of medical treatments is arranged in a decision tree to optimize medical treatment options for both available and future medical treatments.

12. The system of claim 11, wherein a decision tree having an arrangement of medical treatments that preclude use of a future medical treatment is ranked lower than a decision tree having an arrangement that does not preclude the use of a future medical treatment.

13. A computer program product for simulating medical treatment outcomes, the computer program product comprising one or more computer readable storage media collectively having program instructions embodied therewith, the program instructions executable by a processor to:
   receive a request to determine a medical treatment pertaining to a medical condition of a patient;
   apply the request to one or more machine learning models to simulate outcomes for a plurality of different medical treatments for the medical condition, wherein the one or more machine learning models account for impacts of the plurality of different medical treatments on use of medical treatments awaiting future approval, wherein the one or more machine learning models are trained based on data including outcomes of newly available medical treatments and outcomes of new medical treatments awaiting future approval, and wherein accounting, by the one or more machine learning models, for the use of medical treatments awaiting for future approval includes determining whether applying the different medical treatment to the patient precludes the patient from later receiving the medical treatments awaiting future approval; and determine the medical treatment from the simulated outcomes based on a level of impact on the medical treatments awaiting future approval from applying the medical treatment to the patient, wherein the level of impact is based on characteristics of the patient.

14. The computer program product of claim 13, wherein the program instructions are executable to rank a plurality of medical treatments for the request based on the simulated outcomes.

15. The computer program product of claim 13, wherein the one or more models employ a plurality of constraints for the plurality of different medical treatments, wherein the plurality of constraints includes an absolute constraint applied to all patients and a relative constraint that is applied based on the characteristics of patients.

16. The computer program product of claim 13, wherein the plurality of different medical treatments includes a plurality of stages, and the applying the request to one or more models further comprises:

modeling medical treatment options at each stage of a medical treatment to produce simulated outcomes for that medical treatment.

17. The computer program product of claim 13, wherein a plurality of medical treatments is arranged in a decision tree to optimize medical treatment options for both available and future medical treatments.

* * * * *